United States Patent [19]

Carcasona et al.

[11] Patent Number: 5,393,898
[45] Date of Patent: Feb. 28, 1995

[54] METHOD OF PREPARING DIACETYL RHEIN

[75] Inventors: Alfons Carcasona, Cologne; Wolf Grimminger, Bergisch-Gladbach, both of Germany; Pentti Hietala, Helsinki, Finland; Helga Zaeske; Klaus Witthohn, both of Overath, Germany

[73] Assignee: Madaus AG, Cologne, Germany

[21] Appl. No.: 234,583

[22] Filed: Apr. 28, 1994

Related U.S. Application Data

[63] Continuation of Ser. No. 969,242, Feb. 19, 1993, abandoned.

[30] Foreign Application Priority Data

Jun. 25, 1991 [DE] Germany ............................ 4120990

[51] Int. Cl.⁶ ............................................. C07C 50/34
[52] U.S. Cl. .................................................. 552/262
[58] Field of Search ......................... 552/262; 514/510

[56] References Cited

U.S. PATENT DOCUMENTS 4,244,968  1/1981  Friedmann ........................... 424/308

FOREIGN PATENT DOCUMENTS 243968  11/1987  European Pat. Off. .

OTHER PUBLICATIONS

*Merck Index,* 10th ed., 1983, p. 1179.
V. K. Murty et al., Chemical Examination of Cassia Fistula, Tetrahedron, 1967, vol. 23, 515 to 518.
Drugs of the Future, vol. IV, No. 6, 1979.
U. R. Zope et al., A short synthesis of diacerhein, Chemistry and Industry, Communication to the Editor, p. 124, Feb. 15, 1988.

*Primary Examiner*—Howard T. Mars
*Assistant Examiner*—Kimberly J. Kestler
*Attorney, Agent, or Firm*—Felfe & Lynch

[57] ABSTRACT

Diacetylrhein which is substantially free of aloe-emodin components, is prepared by a process wherein
a) rhein-9-anthrone-8-glusoside containing aloe-emodin components is subjected to a liquid-liquid partitioning of the compounds obtained is carried out between a polar organic solvent which is only partly miscible with water and an aqueous phase,
b) the rhein-9-anthrone-8-glucoside contained after the partitioning in the aqueous phase is oxidized to rhein-8-glucoside,
c) the glucose residue in the 8-position of the rhein-8-glucoside is split off in an acidic medium and,
d) the rhein obtained is acetylated and the diacetylrhein recovered.

13 Claims, No Drawings

METHOD OF PREPARING DIACETYL RHEIN

This application is a continuation of application Ser. No. 07/969,242, filed Feb. 19, 1993, now abandoned.

The present invention is concerned with a process for the preparation of diacetylrhein of pharmaceutically usable purity with a residual content of undesired aloe-emodin derivatives of, in all, less than 20 ppm, the diacetylrhein obtainable according to this process and a pharmaceutical composition which contains this compound.

Diacetylrhein of the formula:

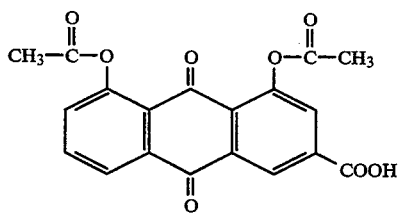

is a medicinally-active compound which possesses anti-arthritic, anti-inflammatory, antipyretic and analgesic activity. Therefore, diacetylrhein is used for the treatment of arthritic diseases (cf., for example DE-A-27 11 493 and U.S. Pat. No. 4,244,968).

Diacetylrhein can be prepared, for example, by the acetylation of barbaloin and oxidation of the peracetylated barbaloin obtained with chromium trioxide. Furthermore, diacetylrhein can be prepared by the acetylation of rhein which can be obtained, for example, from senna drug.

Diacetylrhein obtained according to these processes contains undesired accompanying aloe-emodin derivatives which result from an incomplete oxidation with chromium trioxide or are co-extracted in the case of the extraction of senna drug. These accompanying materials are present in relatively small amounts and can, therefore, only be separated with great difficulty by means of well-known purification procedures. Furthermore, in the case of the first of the above-mentioned processes, chromium residues are present which have to be removed in appropriate manner.

Therefore, it is an object of the present invention to provide a process for the preparation of diacetylrhein which is simple to carry out and gives high yields and in which diacetylrhein is obtained of pharmaceutically usable purity with a residual content of undesired aloe-emodin derivatives of, in all, less than 20 ppm.

Thus, according to the present invention, there is provided a process for the preparation of diacetylrhein, wherein
a) rhein-9-anthrone-8-glucoside containing aloe-emodin components (i. e. aloe-emodin and/or derivatives thereof) is subjected to a liquid-liquid partitioning between a polar organic solvent which is only partly miscible with water and an aqueous phase,
b) the rhein-9-anthrone-8-glucoside contained after the partitioning in the aqueous phase is oxidised to rhein-8-glucoside,
c) the glucose residue in the 8-position of the rhein-8-glucoside is split off in an acidic medium and
d) the rhein obtained is acetylated and diacetylrhein recovered.

Important sources of rhein-9-anthrone-8-glucoside are the sennosides contained in senna drug. A preferred embodiment of the present invention is, therefore, a process for the preparation of diacetylrhein which is substantially free of aloe-emodin components wherein
a) a sennoside mixture is subjected to a reduction to the corresponding rhein-9-anthrone-8-glucoside and aloe-emodin-9-anthrone-8-glucoside compounds,
b) a liquid-liquid partitioning of compounds obtained is carried out between a polar organic solvent which is only partly miscible with water and an aqueous phase,
c) the rhein-9-anthrone-8-glucoside compounds contained in the aqueous phase after partitioning are oxidised to the corresponding anthraquinone compound,
d) the glucose residue in the 8-position of the anthraquinone compound is split off in an acid medium and
e) the 1,8-dihydroxyanthraquinone compound obtained is acetylated and the diacetylrhein recovered.

Reduction of the Sennosides

The sennoside mixture used as starting material can be obtained, for example, from senna drug. The senna drug consists of the dried leaves and fruits of the senna plant, for example of the Indian senna (*Cassia angustifolia*) and the of Egyptian senna (*Cassia acutifolia*). The senna drug contains dianthrone glucosides of rhein and aloe-emodin. The most important ones are sennosides A, B, A1, C, D and D1. The sennosides correspond to the general formula:

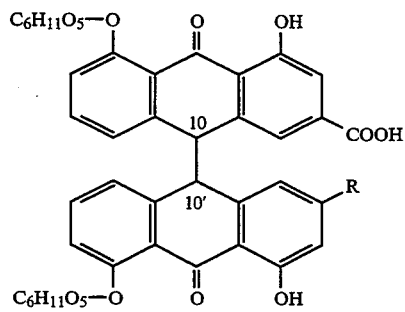

In the case of sennosides A, B and A1, R stands for COOH and in the case of sennosides C, D and D1, R stands for $CH_2OH$. The sennosides A, B and A1 and the sennosides C, D and D1 are stereoisomers and differ from one another by the configuration on carbon atoms 10 and 10'.

The obtaining of sennosides from senna drug is described, for example, in DE-A-32 00 131, reference to which is here made to the complete specification. According to this, the senna drug is first extracted with aqueous methanol. The concentrate remaining after complete removal of the methanol contains the sennosides in the form of the potassium salts. This concentrate can be used as starting material for the process according to the present invention.

The concentrate can also be purified by liquid extraction with alcohols or ketones which are partly soluble in water, for example butan-2-ol or butan-2-one (raffinate). The raffinate is acidified to a pH of about 1.5 to 2.0 and the sennosides are brought to to crystallisation by seeding.

The crude sennoside mixture obtained can also be used as starting material for the process according to the present invention. If desired, the crude sennoside mixture can also be recrystallised.

Alternatively, the concentrated mixed with an alcohol or ketone which is partly soluble in water, especially butan-2-ol, can be used as starting material.

In the case of the extraction of the senna drug, the ratio of drug to extraction solvent is preferably 1:4 to 1:15 and especially 1:4 to 1:10.

The extraction is preferably carried out in the presence of a buffer, for example trisodium citrate, glycine, sodium bicarbonate or saccharose.

According to the process of the present invention, these starting materials are subjected to a complete reduction to give the corresponding rhein-9-anthrone-8-glucoside (R=COOH) and the corresponding aloe-emodin-9-anthrone-8-glucoside (R=CH$_2$OH) of the general formula:

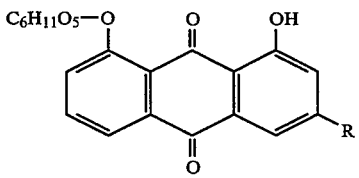

wherein R is COOH or CH$_2$OH.

Reducing agents with an appropriate reducing potential include, for example, stannous chloride, sulphur dioxide, alkali metal borohydrides and preferably alkali metal dithionites, especially sodium dithionite.

For carrying out the reduction, the starting material can be present in aqueous solution or suspension and the reducing agent is added thereto in solid form or dissolved in water. It is also possible to work is a two-phase mixture by adding thereto a polar organic solvent which is partly miscible with water, especially butan-2-ol.

The reduction can be carried out at ambient or higher temperature. The reduction is preferably carried out at 40° to 60° C. and especially at 50° to 55° C. Working is carried out at a weakly acidic to weakly alkaline pH value of the starting sennoside solution or suspension, preferably at pH 7 to 9. If desired, the reduction can be carried out several times and especially 2 to 10 times.

The 9-anthrone-8-glucosides formed are precipitated out by the addition of an acid, for example of sulphuric acid, to a pH value of 4 to 4.5. The temperature should thereby preferably be not more than 40° C. In the case of the precipitating out of the 9-anthrone-8-glucosides and in the case of the isolation thereof, for example by filtration, it is preferable to work under an atmosphere of nitrogen in order to avoid an uncontrolled oxidation of these compounds.

It is important that the reduction proceeds to completion. Therefore, it is preferable to use the reducing agent in large excess. In the case of using sodium dithionite, in general there is employed a 1 to 4 fold amount by weight of sodium dithionite, referred to the content of sennosides in the starting material. Furthermore, the reducing agent is allowed to act for at least 2 hours and preferably for at least 3 hours. In general, the reduction takes place for not more than 10 hours. A post-reduction is preferably carried out under the said conditions.

Before use in the next step, the product obtained is preferably reprecipitated by bringing it into solution by the addition of a base, for example sodium hydroxide or potassium hydroxide, up to a pH of about 6 to 7, the aqueous solution is extracted with butan-2-ol, acetone or butan-2-one and the product is again precipitated out by the addition of an acid to a pH of about 2 to 4.

Liquid-Liquid Partitioning

In this step, the aloe-emodin components and especially aloe-emodin-9-anthrone-8-glucoside are removed. For this purpose, there is carried out a liquid-liquid partitioning of the product obtained between a polar organic solvent which is only partly miscible with water and an aqueous phase. Appropriate polar organic solvents include C$_4$–C$_5$-alkanols and di-C$_1$–C$_3$-alkyl ketones, for example acetone, butan-1-ol, butan-2-ol and butan-2-one, the use of butan-2-ol or acetone being preferred.

To the aqueous phase is preferably added a reducing agent in order to impart a redox potential of $-210$ mV or more negative to the aqueous phase during the whole of the liquid-liquid partitioning. It is preferable to use the same reducing agent as in step a). In the case of using an alkali metal dithionite as reducing agent, in general a 2 to 4% by weight solution at a pH value of from 7 to 11 is sufficient in order to maintain the mentioned potential conditions.

The volume ratio of aqueous phase (heavy phase) to organic phase (light phase) is generally in the range of from 1:5 to 1:40.

The liquid-liquid extraction preferably takes place in countercurrent. The mixture of anthrone compound is thereby isolated in the form of the solution obtained after the reduction or, when the anthrone compounds have been isolated, in the form of a 3 to 15% by weight solution.

After the partitioning, the desired rhein-9-anthrone-8-glucoside is present in the aqueous phase. It is precipitated out by the addition of an acid to give a pH value of about 2 to 4 and recovered in the usual manner.

Oxidation of the Rhein-9-Anthrone-Glucoside

The rhein-9-anthrone-8-glucoside is now oxidised to rhein-8-glucoside of the general formula:

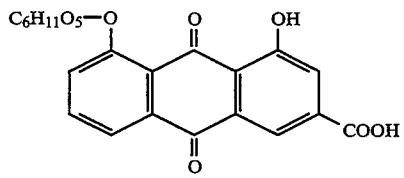

Oxidation agents which can be used for this purpose include, for example, oxygen, peroxide compounds, such as hydrogen peroxide, and manganese, chromium and iron compounds in high oxidation states. It is preferred to use a ferric salt and especially ferric sulphate. It is preferable to work at an elevated temperature but at one below 60° C. In this way, the formation of undesired and undefined oxidation products is avoided. When the oxidation is complete, the rhein-8-glucoside formed is isolated in the usual manner.

Splitting off of the Glucose Residue

The glucose residue in the 8-position is split off in acidic solution. It is preferable to work at a temperature of about 85° to 95° C. The product obtained is isolated in the usual manner.

It is known to convert sennosides, after acidic hydrolysis, by reaction with ferric chloride directly into rhein (see, for example DE-A-27 11 493). However, the yield is thereby only about 10% and, in addition, the rhein formed is difficult to separate.

In the case of the process according to the present invention, the reductive cleavage of the sennosides, the oxidation of the anthrone compounds formed to the corresponding anthraquinone compounds and the splitting off of the glucose residue in the 8-position of the anthraquinone compounds are, in each case, carried out in separate steps. Subsequent to the reductive cleavage, all compounds which, in the further course of the process, could lead to the formation of aloe-emodin or derivatives thereof are quantitatively removed by liquid-liquid partitioning. Furthermore, it is possible to carry out the oxidation at modest temperatures so that the formation of undesired and undefinable oxidation products is avoided. Furthermore, when carrying out the reaction, the iron salt used can be recovered almost quantitatively and, after reoxidising, can be used again. The separation of oxidation step and hydrolysis step permits, on the basis of the greater water solubility of the anthrone glucosides in comparison with the aglycones in question, the gentle carrying out of the oxidation at ambient temperature or below 60° C., the otherwise unavoidable formation of undefined by-products thereby being avoided.

Acetylation of the 1,8-Dihydroxyanthraquinone Compound

The acetylation of the 1,8-dihydroxyanthraquinone compounds obtained takes place in the usual manner. For example, acetylation can be carried out with acetic anhydride in the presence of sodium acetate in the manner described in Arch. Pharm., 241, 607/1903. However, the acetylation can also take place by means of other methods known to the expert, for example by reaction with acetyl chloride or the like.

The diacetylrhein obtained in this manner is substantially free from aloe-emodin and derivatives thereof. The content of these impurities thereby still amounts to about 50 ppm (determined by the analysis process described in the following Examples). The content of these impurities can be further reduced when the diacetylrhein obtained is recrystallised in the following manner: The diacetylrhein is converted into an alkali metal salt by treatment with an appropriate base, an appropriate base being, for example, an alkali metal acetate and preferably potassium acetate. It is preferable to use equimolar amounts of base and an aqueous $C_1$–$C_3$-alcohol, for example 80 to 90% ethanol, as reaction medium. The alkali metal salt of diacetylrhein is allowed to crystallise out in the cold, taken up in an aqueous $C_1$–$C_3$-alcohol and precipitated out by the addition of an acid to a pH value of about 3. The diacetylrhein precipitated out is then isolated in the usual manner and worked up.

The product thus obtained contains less than 20 ppm of the above-mentioned impurities. Furthermore, the product is present in the form of needle-shaped crystals which are especially appropriate for galenical formulation.

The product can be dried in the usual manner. It is preferable first to carry out the drying in a vacuum at a relatively low temperature, for example of not more than 40° C., until the water content of the product has decreased to about 3% or less. Subsequently, the temperature can be increased to 70° to 110° C.

The present invention is also concerned with the substantially pure diacetylrhein obtainable according to the present invention, as well as with pharmaceutical compositions which contain this compound. The fields of use, the dosage to be administered and appropriate forms of dosaging are known from and described, for example, in U.S. Pat. Nos. 4,244,968, 4,346,103, and 4,950,687 and DE-A-27 11 493, as well as in Drugs Exptl. Clin. Res., 6 (1), 53–64/1980.

The following Examples are given for the purpose of illustrating the present invention.

EXAMPLE 1

Obtaining the Sennoside Mixture Used as Starting Material

In each case, 40 kg of senna drug (sennoside content about 1.5%), are introduced into two percolators, connected in series, with a volume of 250 liters and covered with a perforated steel plate. As solvent for the extraction, there is used 70% methanol which is passed to the drug in the first percolator. The solution formed in the first percolator is passed to the drug which is present in the second percolator. The solvent is thereby allowed to flow freely through the first percolator.

For the extraction of 40 kg of senna drug, there is used, in all, 160 liters of solvent. After this volume of 70% methanol has been passed through the two percolators and the corresponding amount of percolate has been collected, the emptying pipe of the percolator is coupled with a post-percolate container and an additional 60 liters of 70% methanol are passed through the percolators. Thereafter, the remaining free solvent from the first percolator is passed into the upper part of the second percolator and the post-percolate is collected until it amounts to 120 liters. The first percolator is then emptied, again filled with 40 kg of senna drug and the post-percolate is pumped on to the drug, the 120 liters of post-percolate thereby sufficing in order to cover the drug in the percolator.

Subsequently, the temperature of the solution is brought to +30° C.

This percolator is connected with the one previously extracted and the extraction is carried out as described above.

For each 40 kg of drug, there are collected 160 liters of percolate from which the methanol is removed in a vacuum rotary evaporator which is equipped with a packed column. There are obtained 30 liters of bottom product. This concentrate is extracted with an equal volume of butan-2-ol saturated with water.

Step a)

Reduction of the Sennosides to Rhein-9-Anthrone-8-Glucosides 1.0 liter of the extracted concentrate is brought to pH 7.5 with 48% aqueous sodium hydroxide solution. The solution is heated to 60° C. and, while stirring, 90 g of sodium dithionite in solid form are added to the solution over the course of half an hour. When the addition is completed, stirring is continued for a further hour. Subsequently, concentrated sulphuric acid is added thereto up to a pH of 2. The solution is cooled to ambient temperature in the course of 2 hours and the crystalline precipitate obtained is filtered off and washed with water containing sulphur dioxide.

If desired, the crude rhein-9-anthrone-8-glucoside is reprecipitated. The still moist filter cake is dissolved in a mixture of 15 parts by volume of butan-2-ol, 85 parts by volume of water which contains 0.5% by weight of sodium pyrosulphite in such a manner that, by means of the addition of a 48% aqueous solution of sodium hydroxide to pH 7, a 10% solution (w/v) is obtained. The solution is acidified with concentrated hydrochloric acid to a pH of 2.8 or below and left to stand for 2 hours. The precipitate obtained is filtered off, washed with water containing sulphur dioxide or sodium pyrosulphite and dried. Yield 90%.

A renewed reduction (post-reduction) is carried out as follows with the product obtained in this manner:

3.0 g of the crude dried rhein-9-anthrone-8-glucoside or the corresponding amount of the moist product are dissolved in 15 ml of water, together with 1.4 g sodium dithionite and 2.3 ml 5 N aqueous sodium hydroxide solution. Subsequently, it is made up with water to 24 ml and the solution is heated to 55° C. for 20 minutes. Thereafter, a further 1.5 g of sodium dithionite are added to the solution and heated for 20 minutes at 55° C. Subsequently, 0.9 ml of 5 N aqueous sodium hydroxide solution and 1.5 g of sodium dithionite are added thereto. After heating for 20 minutes to 55° C., 0.9 ml of 5 N aqueous sodium hydroxide solution are again added thereto. The solution obtained is introduced directly into the following liquid-liquid extraction.

Step b)

Separation of the Aloe-Emodin Components

The separation of the aloe-emodin components takes place by liquid-liquid partitioning of the anthrone-8-glucosides in countercurrent with the help of an apparatus containing 60 mixing-settler units. As aqueous heavier phase, there is used a solution of 3.0 g of sodium dithionite in 3.5 ml of 5 N aqueous sodium hydroxide solution and 96 ml of water. As organic lighter phase, there is used butan-2-ol or acetone saturated with water. The two phases are supplied to the apparatus in such a manner that the volume ratio of heavier phase to lighter phase is 1:10.

The mixture to be separated is supplied to the apparatus in the form of the freshly produced solution or in the form of a solution of corresponding pH value and of corresponding concentration which contains the 9-anthrone-8-glucosides obtained from step a) in such a manner that 30 parts by volume of the organic phase are used per part by volume of the mixture to be separated.

The pH of the solution containing the mixture is maintained at 9 to 9.5 with the help of a glycine buffer. The buffer comprising 3 parts by volume of a 7.5% glycine solution and 1 part by volume of 1 N aqueous sodium hydroxide solution is added in an amount of 240 ml of buffer solution per 150 g of crude rhein-9-anthrone-9-glucoside. The undesired aloe-emodin compounds enrich in the organic phase, whereas the rhein-9-anthrone-8-glucoside remains in the aqueous phase. The aqueous phase is acidified with sulphuric acid to pH 2.8 and the precipitate formed is filtered off and washed with water and acetone and dried in air at ambient temperature. In this way, rhein-9-anthrone-8-glucoside is obtained with a content of aloe-emodin components of 41 ppm, determined as aloe-emodin according to the method which is described at the end of this description. Yield 97%, referred to the rhein-9-anthrone-8-glucoside.

Step c)

Oxidation to Rhein-8-Glucoside

The product from step b) (referred to a content of 3.0 kg of sennosides A, A1 and B) is suspended in a solution of 185 liters of demineralised water and 75.5 kg of ferric sulphate hydrate (22% $Fe^{3+}$). The suspension is heated to 55° to 62° C. and oxidised for 14 hours with the use of a rapidly running disperser. When the oxidation is complete, the rhein-8-glucoside formed is filtered off and washed with 50 liters of demineralised water which has been adjusted to pH 2 with sulphuric acid.

Step d)

Hydrolysis to Rhein

The moist filter residue from step c) is suspended in 200 kg of 20% by weight sulphuric acid and stirred for 8 hours at 88° to 92° C. The rhein formed is filtered off and, for storage, can be dried at 1 mbar vacuum for 48 hours at 40° C. or can be used immediately in a moist state for the acetylation in step e).

The total yield for steps a) to d) is 79%, referred to the sennosides A, A1 and B used in step a).

Step e)

Acetylation to Give Diacetylrhein 6.5 kg of rhein from step d) are suspended in 100 liters of acetic anhydride for 10 minutes, mixed with 2 kg of potassium acetate, heated to 95° C. while stirring, mixed with 0.65 kg of activated carbon and stirred for 30 minutes at 90° to 95° C. The activated carbon is filtered from the hot solution and the filtrate is mixed at 90° C. with 2.1 kg of 96 to 98% by weight sulphuric acid. Subsequently, while stirring, it is cooled as quickly as possible to 20° C. and the resulting suspension is filtered. The residue is washed free of sulphate with demineralised water. The yield is 83%.

Step f)

Recrystallisation, Drying and Grinding

With rapid stirring, 7.5 kg of diacetylrhein from step e) (referred to the dry substance) are suspended in 375 liters of 90% by volume ethanol. The suspension is heated to 70° C. and then mixed with 3.75 kg of potassium acetate. Upon cooling to 0° to 2° C., the pure potassium salt of diacetylrhein crystallises out from the clear solution which has, in the meantime, formed. The potassium salt is filtered off and dissolved in 300 liters of 40% by volume ethanol at 20° to 30° C. with the addition of 3 kg potassium acetate. The clear solution is adjusted with 10% by weight sulphuric acid to pH 3.0. The diacetylrhein which crystallises out is filtered off and washed free of sulphate with demineralised water.

The product is first dried in a vacuum at 1 mbar and 40° C. within the course of 24 hours. When the residual water content has decreased to below 3%, the material is coarsely comminuted and further dried at 1 mbar vacuum and 70° C. for 24 hours. Subsequently, it is ground to a sieving size of 0.5 mm and again dried at 1 mbar vacuum and 70° C. for the removal of solvent residues. The yield from step f) is 95%.

EXAMPLE 2

The extraction of the senna drug and the reduction of the sennosides described in Example 1 is repeated. The subsequent reduction is then carried out as follows:

140 g saccharose, 4.5 g 85% sodium dithionite and 13.3 g potassium acetate are dissolved in 133 ml of water and 1.3 ml of 48% sodium hydroxide solution and 17.3 g potassium carbonate are added thereto. Subsequently, the reaction mixture is mixed with 293 ml acetone and 50 ml of water. The mixture is shaken in a separating funnel and the phases are separated, 375 ml of upper phase (acetone phase) and 130 ml of lower phase thereby being obtained.

In 98 ml of the lower phase are dissolved 1.4 ml of a 48% sodium hydroxide solution and 10 g of crude rhein-9-anthrone-8-glucoside. The solution is warmed to 45° to 50° C. and maintained at this temperature for 20 C to 30 minutes. Subsequently, 1.0 ml of a 48% sodium hydroxide solution and 3.4 g of sodium dithionite are added thereto and heated for a further 20 to 30 minutes to 45° to 50° C. Subsequently, there are again added thereto 1.0 ml of 48% sodium hydroxide solution and 3.4 g of sodium dithionite, followed by heating to 45° to 50° C. for 20 to 30 minutes.

The separation of the aloe-emodin components takes place by liquid-liquid partitioning of the reduced solution in countercurrent against the above-mentioned upper phase (acetone phase). The raffinate phase flowing off and containing the rhein-9-anthrone-8-glucoside is concentrated to 400 ml and mixed with 20 ml butan-2-ol.

Hydrochloric acid or sulphuric acid is added thereto up to a pH value of 4.0 to 4.2. The precipitate formed is filtered off, washed with 40 ml of water and 30 ml of acetone and subsequently dried. The subsequent oxidation takes place in the manner described in Example 1.

EXAMPLE 3

The concentrate obtained after extraction of the senna drug is mixed with about 2 liters of butan-2-ol. The reduction of the mixture of senna fruit concentrate and butan-2-ol is then carried out in 7 steps under nitrogen as protective gas. After reduction step I, there follows a precipitation of the crude rhein-9-anthrone-8-glucoside.

Reduction Step I 100 liters of a mixture of senna fruit concentrate and butan-2-ol containing about 4 kg of sennosides are placed in a stirrer container and covered with nitrogen. While stirring, 6 liters of a 20% by weight aqueous solution of sodium hydroxide and thereafter 350 liters of water-saturated butan-2-ol, for example from step II, are successively added thereto and stirred for 15 minutes. The batch is heated to 42 to 50° C., mixed with 7 kg sodium dithionite and further stirred for 45 minutes. The pH value is maintained at 7.5 to 8 with 20% by weight aqueous sodium hydroxide solution. The reduction potential (against an Ag/AgCl electrode) is, if necessary, maintained below −630 mV by the addition of sodium dithionite. After cooling to 30° to 35° C., precipitation is carried out within 1.5 hours with 10% by weight of sulphuric acid to pH<4. The resultant suspension is stirred for about 10 hours at <25° C. with a slow speed of stirring and the resultant precipitate is filtered off. The precipitate is suspended in 60 liters of 15% by weight butan-2-ol, stirred for 30 minutes at 50° to 60° C. and subsequently filtered. The residue is washed with 100 liters of demineralised water. The crude yield of rhein-9-anthrone-8-glucoside is more than 82%, referred to the sennosides used.

Reduction Step II 3.3 kg crude rhein-9-anthrone-8-glucoside from step I are suspended in a mixture of 42 liters of demineralised water and 7.4 liters of butan-2-ol. The suspension is brought into solution with 2 liters of 20% by weight aqueous sodium hydroxide solution and 9.9 kg trisodium citrate and thereafter mixed with 3.3 kg sodium dithionite and 350 liters of water-saturated butan-2-ol, for example from step III. The batch is heated to 42° to 45° C., the pH value being maintained at 8.5 to 9 with 20% by weight aqueous sodium hydroxide solution. The reduction potential (against Ag/AgCl electrode) is, if necessary, maintained below −750 mV by the addition of sodium dithionite. After standing for 30 minutes, the upper phase is removed and the lower phase further worked up in step III.

Reduction Step III

The reduction/extraction process described in step II is repeated with the lower phase from step II, with the addition of the following chemicals:
1.65 kg sodium dithionite
0.8 liters 20% by weight sodium hydroxide solution and
350 liters of water-saturated butan-2-ol, for example from step IV.

Reduction Steps IV and VII

The reduction/extraction process described in step II is repeated with the lower phase from the preceding step in question with the addition of the following chemicals:
0.825 kg sodium dithionite
0.4 liters 20% by weight aqueous sodium hydroxide solution and
350 liters of water-saturated butan-2-ol, for example from the following steps in question using the countercurrent principle.

The lower phase separated off in step VII is cooled to 30° to 35° C. and the rhein-9-anthrone-8-glucoside is precipitated out as described in step I. The resultant precipitate is filtered off and washed with 100 liters of demineralised water. Subsequently, it is covered with 10 liters of ferric sulphate solution (preparation see step b, Example 1).

The rhein-9-anthrone-8-glucoside is then converted into the sennosides in the manner described in Example 1 or 2.

Pharmacological investigations

The effectiveness of diacetylrhein was determined in chronic inflammation models after oral administration.

The following experimental models were used: cotton pellet granuloma in rats and arthrosis in rabbits induced by the intraarticular administration of vitamin A.

A) Cotton Pellet Granuloma In Rats

Young sexually mature rats (n=10) were given 25, 50 or 100 mg diacetylrhein/kg or 5 mg indomethacin/kg or 100 mg acetylsalicylic acid/kg daily for 5 days. A control group only treated with water was also used. Implantation of the pellets took place on the first day of treatment. Fresh and dry weights of the granuloma prepared at the end of the experiment showed a significant and clearly dosage-dependent reduction in comparison with the control group. The action of 100 mg diacetylrhein/kg thereby corresponded to about the action of 5 mg indomethacin or of 100 mg acetylsalicylic acid. The weights of the thymus and adrenals did not change during the treatment.

B) Vitamin A Arthrosis

An arthrosis-like joint change was initiated in two groups each of 10 rabbits (white New Zealanders) by means of three intraarticular injections of 30,000 IU of vitamin A over the course of 9 days. 56 days later, 10 animals were treated with 3 mg of diacetylrhein/kg/day for 8 weeks. In comparison with the control group, the macroscopically and microscopically recognisable joint changes in the treatment group were significantly reduced.

Furthermore, the curative action of diacetylrhein was compared with that of acetylsalicylic acid on each of 7 rabbits which, after 6 days pre-treatment with three times 10,000 IU vitamin A and a 26 day treatment-free interval for 8 weeks, received either 5 mg of diacetylrhein/kg/day (experimental group), 15 mg of acetylsalicylic acid/kg/day (positive control group) or remained untreated (negative control group). In all three groups, 24 days after the last vitamin A injection, comparable disturbances of movement occurred in the form of dragging of the rear legs. In the negative control group, during the following 8 weeks, the clinical signs of a manifest arthrosis increased. In the experimental group and the positive control group, these symptoms improved significantly during the 8 weeks of treatment.

Gastric Mucosa Changes

Whereas a single administration of 400 mg of diacetylrhein/kg or of the solvent did not give rise to any erosions of the gastric mucosa in the case of the rat, after the administration of ibuprofen (200 mg/kg) or of indomethacin (20 mg/kg), there were found distinct mucosal damages in the form of punctiform (1 mm diameter) to large (3 mm diameter) erosions. Also the twice daily administration of 100 mg of diacetylrhein/kg over the course of 3 days also did not initiate any mucosal damage, whereas the corresponding use of 10 mg of indomethacin/kg certainly did: the erosions thereby having a diameter of 1 to 3 mm.

Toxicology

The acute toxicity $LD_{50}$ was, depending upon the species investigated (rat, mouse, cat), after the oral administration 1.9 to 7.9 g/kg. The rat thereby proved to be the least sensitive. After parenteral administration (i.v. or i.p.), the $LD_{50}$ values in the case of these species was from 119 to 339 mg/kg.

Clinical Investigations

1. The action of diacetylrhein was investigated in coxarthrosis and gonarthrosis in 95 (49/46) patients in a double-blind study against naproxen and subsequent placebo after-treatment. The dosage administered was 50 mg of diacetylrhein twice daily or 750 mg of naproxen daily. The period of treatment was 60 days after a 7 day wash-out phase. The subsequent placebo treatment extended over 60 days.

Test parameters were the pain and movement symptoms according to a score scale, function limitation and compatibility.

In both treatment groups (diacetylrhein/naproxen), with regard to all test parameters there was ascertained a statistically significant rate of improvement ($P<0.01$ and $P<0.05$, respectively) in comparison with the initial values. After discontinuation of the treatment and subsequent administration of placebo, there was shown, however, on days 90 and 120 with regard to the parameters of spontaneous pain and active and passive movement pain, a statistically significant superiority ($P<0.01$) in comparison with the naproxen/placebo collective. On the 5% level, this difference was also verified for the variable night pain and pressure pain 30 days after discontinuation of diacetylrhein.

2. In an open running study with control, there was investigated the action of diacetylrhein against osteoarthrosis of the spine and of the knee in 70 patients (35/35). The dosage administered was 100 mg of diacetylrhein per day. The period of treatment was 60 days and the period of observation was 75 days. The test parameters were pain and movement limitation. The parameters were evaluated according to a score system.

The control group comprised 35 patients in the case of which exclusively physiotherapeutic measures were carried out. Physiotherapy was also carried out in the diacetylrhein treatment group.

With regard to all parameters, the evaluation of the results showed a statistically significant superiority of the treatment group with regard to the control group. Also after discontinuation of the treatment, a continuing therapeutic effect (hang-over effect) could be ascertained for the diacetylrhein group.

3. The action of diacetylrhein in the case of localised arthrosis in 20 patients was investigated in a single blind crossover study against naproxen. The patients were divided up into two groups: in the first group, initially 50 mg of diacetylrhein was administered twice daily for 20 days. Subsequently, there followed a three day wash-out phase and a further treatment with 250 mg of naproxen twice daily for a further 20 days. In the second group, the reverse sequence was used. The period of treatment was, in all, 43 days. The test parameters of pain, compression pain, passive movement pain, function limitation and swelling were determined according to a score system.

The evaluation of the results showed a superiority of the treatment with diacetylrhein in comparison with the treatment with naproxen. No noteworthy side effects were observed and also no changes of the clinical laboratory parameters.

4. The action of diacetylrhein was investigated in 23 patients (12/11) with osteoarthrosis in a randomised double blind study using the "double dummy technique" (compatibility study). The dosage administered was 50 mg of diacetylrhein twice daily and 250 mg of naproxen three times daily. The period of treatment was 4 weeks. The test parameters were the oesophagogastroduodenoscopic findings before and after the therapy. Only patients with normal mucosal findings or with slight mucosal lesions (grade 1) were used in the study.

After 4 weeks, the endoscopic findings showed, in one case (10%) in the diacetylrhein group, mucosal lesions of grade 2, whereas in the naproxen treatment group 5 patients (50%) showed mucosal lesions of grade 2, 3 and 4. In all cases, a normal take-up finding was present.

Analytical Determination of Aloe-Emodin 50 mg of diacetylrhein are dissolved in 25.3 ml of 0.5 M aqueous sodium hydroxide solution in a separating funnel and shaken for 10 minutes. Subsequently, 74.6 ml of a solution are added thereto which contains 0.5 M glycine and 0.5 M sodium chloride, a pH value of 9.5 thereby being obtained.

This solution is extracted three times with 25 ml of chloroform. The combined organic phases are extracted once with 10 ml 0.5 M of a buffer of pH 9.5 (glycine, sodium hydroxide and sodium chloride) and once with 10 ml 0.01 M sulphuric acid. The solvent is removed from the organic phase and the residue is dissolved in 1 ml methanol.

For a standard solution, 2 mg of aloe-emodin are dissolved in 20 ml of N,N-dimethylacetamide and diluted with methanol to a concentration of 2 μg/ml, corresponding to 40 ppm.

The content of the solutions is investigated by HPLC. The linearity of the HPLC method was demonstrated with aloe-emodin standard solution in the range of from 0.11 μg/ml (corresponding to 2.2 ppm) to 53.6 μg/ml (corresponding to 1072 ppm). The content determination takes place with a Merck HPLC column Lichrocart 250-4, packed with LiChrospher-100 RP-18, 5 μm, at 40° C. with a mobile phase of 1% acetic acid in methanol (v/v), 1% acetic acid in water (v/v) and acetonitrile in a ratio of 49:46:5.

Analytical Determination of the Product of Step B), Namely, Rhein-9-Anthrone-8-Glucoside With a Content of Aloe-Emodin Components of 41 PPM, Determined as Aloe-Emodin The substance to be investigated is converted into rhein and aloe-emodin by oxidation with ferric chloride with simultaneous hydrolysis with hydrochloric acid in a two-phase mixture of aqueous solution and carbon tetrachloride. The rhein is converted into a salt so that it can be separated from the aloe-emodin by liquid-liquid partitioning. The aloe-emodin present in the organic phase is determined by HPLC.

We claim:

1. The method of preparing diacetylrhein which is substantially free of aloe-emodin components, which comprises:
    a) admixing a mixture of rhein-9-anthrone-8-glucoside and aloe-emodin-9-anthrone-8-glucoside with an aqueous solution having a pH of 6.5 to 7.5 and with a polar organic solvent which is incompletely miscible with water,
    b) subjecting the resulting mixture to liquid-liquid partitioning to form a light organic phase containing said aloe-emodin-9-anthrone-8-glucoside and a heavy aqueous phase containing said rhein-9-anthrone-8-glucoside,
    c) separating said aqueous phase from said organic phase,
    d) oxidizing the rhein-9-anthrone-8-glucoside contained in said aqueous phase to rhein-8-glucoside,
    e) treating said rhein-8-glucoside with an acid to remove the glucose in the 8-position and form substantially pure rhein,
    f) acetylating said rhein to form substantially pure diacetylrhein, and
    g) recovering said diacetylrhein.

2. The method of claim 1, wherein the polar organic solvent is acetone or butan-2-one.

3. The method of claim 1, wherein the redox potential of the aqueous phase employed in the liquid-liquid partitioning is −210 MV or more negative.

4. The method of claim 1, wherein the liquid-liquid partitioning is performed in countercurrent fashion.

5. The method of claim 1, wherein said rhein-9-anthrone-8-glucoside is oxidized to rhein-8-glucoside with a ferric salt.

6. The method of claim 5, wherein said ferric salt is ferric sulfate.

7. The method of preparing diacetylrhein which is substantially free of aloe-emodin components, which comprises
    a) reducing a sennoside mixture to form a mixture of rhein-9-anthrone-8-glucoside and aloe-emodin-anthrone-8-glucoside,
    b) admixing said mixture of rhein-9-anthrone-8-glucoside and aloe-emodin-9-anthrone-8-glucoside with an aqueous solution having a pH of 6.5 to 7.5 and with a polar organic solvent which is incompletely miscible with water,
    c) subjecting the resulting mixture to liquid-liquid partitioning to form a light organic phase containing said aloe-emodin-9-anthrone-8-glucoside and a heavy aqueous phase containing said rhein-9-anthrone-8-glucoside,
    d) separating said aqueous phase from said organic phase,
    e) oxidizing the rhein-9-anthrone-8-glucoside contained in said aqueous phase to rhein-8-glucoside,
    f) treating said rhein-8-glucoside with an acid to remove the glucose in the 8-position and form substantially pure rhein,
    g) acetylating said rhein to form substantially pure diacetylrhein, and
    h) recovering said diacetylrhein.

8. The method of claim 7, wherein said sennoside mixture is reduced with an alkali metal dithionite.

9. The method of claim 8, wherein the reduction of said sennoside mixture is performed at a pH of 7 to 9.

10. The method of claim 7, wherein the reduction of the sennoside mixture is repeated several times.

11. The method of claim 7, wherein said sennoside mixture is obtained by extracting senna drug with aqueous methanol.

12. The method of claim 11, wherein the extraction with methanol is performed in the presence of a buffer.

13. The method of claim 1 or 7, which further comprises recrystallizing said substantially pure diacetylrhein by
    a) converting it into an alkali metal salt,
    b) dissolving said alkali metal salt in an aqueous alkanol of 1 to 3 carbon atoms, and
    c) precipitating the diacetylrhein by adding an acid to the alkanol solution.

* * * * *